United States Patent
Umeda et al.

(10) Patent No.: US 10,653,825 B2
(45) Date of Patent: May 19, 2020

(54) METHOD FOR PRIMING HOLLOW-FIBER MEMBRANE MODULE

(71) Applicant: KANEKA CORPORATION, Osaka-shi, Osaka (JP)

(72) Inventors: Nobuyoshi Umeda, Settsu (JP); Shuhei Taniguchi, Settsu (JP)

(73) Assignee: KANEKA CORPORATION, Osaka-Shi (JP)

(*) Notice: Subject to any disclaimer, the term of this patent is extended or adjusted under 35 U.S.C. 154(b) by 301 days.

(21) Appl. No.: 15/581,259

(22) Filed: Apr. 28, 2017

(65) Prior Publication Data
US 2017/0232180 A1     Aug. 17, 2017

Related U.S. Application Data

(63) Continuation of application No. PCT/JP2015/079412, filed on Oct. 19, 2015.

(30) Foreign Application Priority Data

Oct. 31, 2014  (JP) ................. 2014-222971

(51) Int. Cl.
| | |
|---|---|
| *A61M 1/36* | (2006.01) |
| *B01D 63/02* | (2006.01) |
| *B01D 65/00* | (2006.01) |
| *A61M 1/34* | (2006.01) |
| *B01D 67/00* | (2006.01) |
| *A61M 1/02* | (2006.01) |

(52) U.S. Cl.
CPC ........ *A61M 1/3643* (2013.01); *A61M 1/0259* (2013.01); *A61M 1/34* (2013.01); *B01D 63/02* (2013.01); *B01D 65/00* (2013.01); *B01D 67/0088* (2013.01)

(58) Field of Classification Search
CPC ...... C12M 41/46; C12M 41/44; C12M 41/48; C12M 33/04; C12M 27/00; C08L 25/06; C08L 67/02; C08L 23/12; B01D 69/02; B01D 69/043
See application file for complete search history.

(56) References Cited

U.S. PATENT DOCUMENTS

| | | |
|---|---|---|
| 2005/0203493 A1 | 9/2005 | Kuroda et al. |
| 2012/0031840 A1 | 2/2012 | Kitaguchi et al. |
| 2014/0287502 A1 | 9/2014 | Taniguchi |

FOREIGN PATENT DOCUMENTS

| | | | |
|---|---|---|---|
| JP | 2004-81833 A | 3/2004 | |
| JP | 2009-268762 A | 11/2009 | |
| JP | 2011-212262 A | 10/2011 | |
| JP | 2012-16595 A | 1/2012 | |
| WO | WO9640320 A1 * | 12/1996 | ............ A61M 1/36 |
| WO | WO 2013/061859 A | 5/2013 | |

OTHER PUBLICATIONS

International Search Report for PCT/JP2015/079412 dated Jan. 12, 2016.

* cited by examiner

*Primary Examiner* — Satyendra K Singh
(74) *Attorney, Agent, or Firm* — Birch, Stewart, Kolasch & Birch, LLP

(57) ABSTRACT

Provided is a priming method including a step of filling a priming liquid in a hollow-fiber membrane module in which hollow-fiber membranes are packed in a vessel having an inlet port, an outlet port, and a filtrate discharge port at a linear velocity of 20 cm/min or more and 550 cm/min or less through the inlet port or the outlet port in an amount of 15% or more relative to a volume of the hollow-fiber membrane module. According to the present invention, the effective filtration area at the time of cell suspension treatment is increased, and the recovery rate of cells and the filtration rate can be improved. Further, since the cell treatment can be completed while maintaining the closed environment, the obtained cells can be provided for therapeutic applications.

10 Claims, 2 Drawing Sheets

METHOD FOR PRIMING HOLLOW-FIBER MEMBRANE MODULE

CROSS-REFERENCE TO RELATED APPLICATIONS

The present application is a continuation of International Application No. PCT/JP2015/079412 filed Oct. 19, 2015, published on May 6, 2016, which claims priority from Japanese Patent Application No. 2014-222971 filed Oct. 31, 2014, all of which are incorporated herein by reference.

TECHNICAL FIELD

The present invention relates to a technique for priming a hollow-fiber membrane module in which hollow fiber membranes are packed.

BACKGROUND ART

A hollow-fiber membrane module packed with hollow fiber membranes is widely used for the purpose of separating and filtering proteins, viruses, and contaminants in a cell suspension in blood purification or plasma skimming in the field of extracorporeal circulation, or in the field of cell therapy. In a case where a hollow-fiber membrane module is used in the field of extracorporeal circulation, since the blood that has passed through the hollow-fiber membrane module returns directly into the body, it is required to completely remove the air and air bubbles filled in the hollow-fiber membrane module in advance, and "priming" for introducing a priming liquid such as physiological saline into the hollow-fiber membrane module is performed before starting the extracorporeal circulation (Patent Literature 1). However, in order to fill the whole hollow-fiber membrane module with priming liquid, the priming liquid is introduced from the inside and the outside of the hollow fiber membrane, that is, from both the blood channel side and the dialysate side by the different flow paths, therefore, in the process, the switching of the flow paths is complicated and takes a long time.

On the other hand, the priming method in the case of using the hollow-fiber membrane module in the field of cell therapy has not been considered at all (Patent Literature 2). This is because in the field of cell therapy, being different from extracorporeal circulation, the cell suspension that has passed through the hollow-fiber membrane module does not return directly into the body, therefore, it is not required to completely remove the air and air bubbles in the hollow-fiber membrane module in advance, and it is considered that the necessity of the consideration for performing the priming was low. However, in order to efficiently separate and filter proteins, viruses, and contaminants in the cell suspension, it is required to treat the cells in a state that both the inside and the outside of the hollow fiber membrane are wet, therefore, the process of the "priming" in which the inside and the outside of the hollow fiber membrane are filled with a priming liquid, such as physiological saline, before starting the treatment of cells, and the effective filtration area of the hollow fiber membrane is enlarged, contributes to the improvement of the filtration rate and the improvement of the cell recovery rate, and therefore, is extremely important. Further, in a case where the hollow-fiber membrane module is used in cell therapy applications, being different from blood purification, it is difficult to assume that the priming liquid is introduced from the outside of the hollow fiber membrane, but from the viewpoint of bringing the priming liquid into contact with the hollow fiber membrane rapidly, there were some cases where the priming liquid is introduced from the outside of the hollow fiber membrane through a large-diameter opening. Accordingly, also in the cell therapy applications, a priming method in which the priming liquid introduced from the inside of the hollow fiber membrane can be filled into both the inside and the outside of the hollow fiber membrane is required, but as described above, such a method has not been considered at all in the past, and in order to realize this, there was no choice but to devise the structure of the hollow-fiber membrane module, for example, an air release valve is provided in the outside of the hollow fiber membrane, and the air existing in the outside of the hollow fiber membrane is released.

Patent Document 1: Japanese Unexamined Patent Application, Publication No. 2009-268762

Patent Document 2: PCT International Publication No. 2013/061859

DISCLOSURE OF THE INVENTION

Problems to be Solved by the Invention

An object of the present invention is to solve the problems in the method for priming a hollow-fiber membrane module described above. Specifically, an object of the present invention is in priming a hollow-fiber membrane module in an arbitrary shape, to provide a priming method in which the priming liquid introduced only from the inside of the hollow fiber membrane can be easily filled into both the inside and the outside of the hollow fiber membrane.

In addition, another object of the present invention is to provide a method for producing a cell concentrate from a cell suspension in a short time efficiently, using a hollow-fiber membrane module to which the priming method has been applied.

Means for Solving the Problems

As a result of the intensive study to solve the problems described above, the present inventors have found a priming method in which the priming liquid introduced from the inside of the hollow fiber membrane can be easily filled into both the inside and the outside of the hollow fiber membrane by designing the linear velocity of the priming liquid to be introduced into a hollow-fiber membrane module in a specific range, in priming the hollow-fiber membrane module in an arbitrary shape, and thus have completed the present invention.

That is, the gist of the present invention is as follows.

(1) A method for priming a hollow-fiber membrane module in which hollow-fiber membranes are packed in a vessel having an inlet port, an outlet port, and a filtrate discharge port, including filling a priming liquid in the hollow-fiber membrane module in an amount of 15% or more relative to a volume of the hollow-fiber membrane module at a linear velocity of 20 cm/min or more and 550 cm/min or less from the inlet port or the outlet port of the hollow-fiber membrane module.

(2) The method for priming a hollow-fiber membrane module described in the above (1), in which a pressure difference between internal pressure and external pressure of a hollow fiber membrane at the time of priming is 7 mmHg or more and 29 mmHg or less.

(3) The method for priming a hollow-fiber membrane module described in the above (2), in which the internal pressure is negative pressure.

(4) The method for priming a hollow-fiber membrane module described in any one of the above (1) to (3), in which the linear velocity is 35 cm/min or more and 450 cm/min or less.
(5) The method for priming a hollow-fiber membrane module described in any one of the above (1) to (4), in which the priming liquid is filled in the hollow-fiber membrane module in an amount of 70% or more relative to a volume of the hollow-fiber membrane module.
(6) The method for priming the hollow-fiber membrane module described in any one of the above (1) to (5), in which the priming liquid is introduced into the inside of the hollow fiber membrane.
(7) The method for priming a hollow-fiber membrane module described in any one of the above (1) to (6), in which the inlet port and the outlet port communicate with each other through the inside of the hollow fiber membrane.
(8) The method for priming a hollow-fiber membrane module described in any one of the above (1) to (7), in which the hollow fiber membrane has pores with a pore diameter of 0.07 μm or more and 1.5 μm or less.
(9) The method for priming a hollow-fiber membrane module described in any one of the above (1) to (8), in which the priming liquid is at least one selected from the group consisting of physiological saline, infusion, serum, and a medium.
(10) A method for producing a cell concentrate, including, after applying the method for priming a hollow-fiber membrane module described in any one of the above (1) to (9) and (14) to the hollow-fiber membrane module, introducing a cell suspension into the hollow-fiber membrane module from an inlet/outlet port of the hollow-fiber membrane module, and concentrating the cell suspension while discharging a filtrate containing no cells from the filtrate discharge port.
(11) The method for producing a cell concentrate described in the above (10), wherein the hollow-fiber membrane module provided with the filtrate discharge port, the number of which is at least one, is used.
(12) The method for producing a cell concentrate described in the above (10) or (11), in which the cell suspension is introduced into the hollow-fiber membrane module from the inlet/outlet port of the hollow-fiber membrane module at a linear velocity of 500 cm/min or more and 2000 cm/min or less.
(13) The method for producing a cell concentrate described in the above (12), in which the cell suspension is derived from the hollow-fiber membrane module through the filtrate discharge port at a filtration rate of 1500 mL/m$^2$/min or more and 3750 mL/m$^2$/min or less.
(14) The method for priming a hollow-fiber membrane module described in any one of the above (1) to (9), in which the linear velocity is 35 cm/min or more and 300 cm/min or less.

Effects of the Invention

According to the priming method of the present invention, the effective filtration area of the hollow-fiber membrane module at the time of cell treatment is enlarged, and the filtration rate is improved without causing the lowering of the cell recovery rate, which is generated in the case where the priming is insufficient, and further, the cell recovery rate can be improved without lowering the filtration rate. Furthermore, in the priming method of the present invention, there is no need to devise the structure of the hollow-fiber membrane module, therefore, suitable priming can be performed, for example, even in the hollow-fiber membrane module without having an air release valve in the outside of the hollow fiber membrane. Further, in the hollow-fiber membrane module without having the air release valve, which has been treated by the priming method of the present invention, the cell treatment can be completed while maintaining a closed environment, therefore, the cells obtained can be provided for therapeutic applications.

PREFERRED MODE FOR CARRYING OUT THE INVENTION

Hereinafter, the present invention will be described.
The priming method of the present invention is a method for priming a hollow-fiber membrane module in which hollow-fiber membranes are packed in a vessel having an inlet port, an outlet port, and a filtrate discharge port.
The hollow-fiber membrane module used in the present invention is a type of module in which hollow fiber membranes are packed in a vessel having an inlet port, an outlet port and a filtrate discharge port. In the hollow-fiber membrane module, a priming liquid is introduced into the inside of the hollow fiber membrane from the inlet port (or outlet port). While filling the space of the inside of the hollow fiber membrane with the priming liquid, part of the priming liquid is discharged to the outside of the hollow fiber membrane passing through the micropores arranged on the wall of the hollow fiber membrane, and the priming liquid is filled in the space between the vessel and the hollow fiber membranes. Further, the priming liquid of the inside of the hollow fiber membrane is discharged through the outlet port (or the inlet port), and the priming liquid discharged to the outside of the hollow fiber membranes is discharged through the filtrate discharge port from the hollow-fiber membrane module in the form of replacement with a cell suspension.
In addition, the inlet port and the outlet port communicate with each other through the inside of the hollow fiber membrane. With such a configuration, a liquid such as a cell suspension passes through the hollow portion inside the hollow fiber membrane from the inlet port, and is derived to the outside of the hollow-fiber membrane module from the outlet port, for example, when the cell suspension passes through the inside of the hollow fiber membrane, the liquid components move outward through the hollow fiber membrane wall, and the cell concentration can be performed.
In addition, the inlet port of the priming liquid to be introduced into the hollow-fiber membrane module in a priming process may become the outlet port of the cell suspension to be introduced in the subsequent cell concentration process, therefore, in the present invention, one port of the inlet and outlet ports for a liquid to be filtered is designated as an "inlet port", and the other port is designated as an "outlet port".
However, in the following description, the port for introducing the priming liquid into the hollow-fiber membrane module will be described as an "inlet port", and the port for deriving the priming liquid from the hollow-fiber membrane module will be described as an "outlet port".

Figure 1:
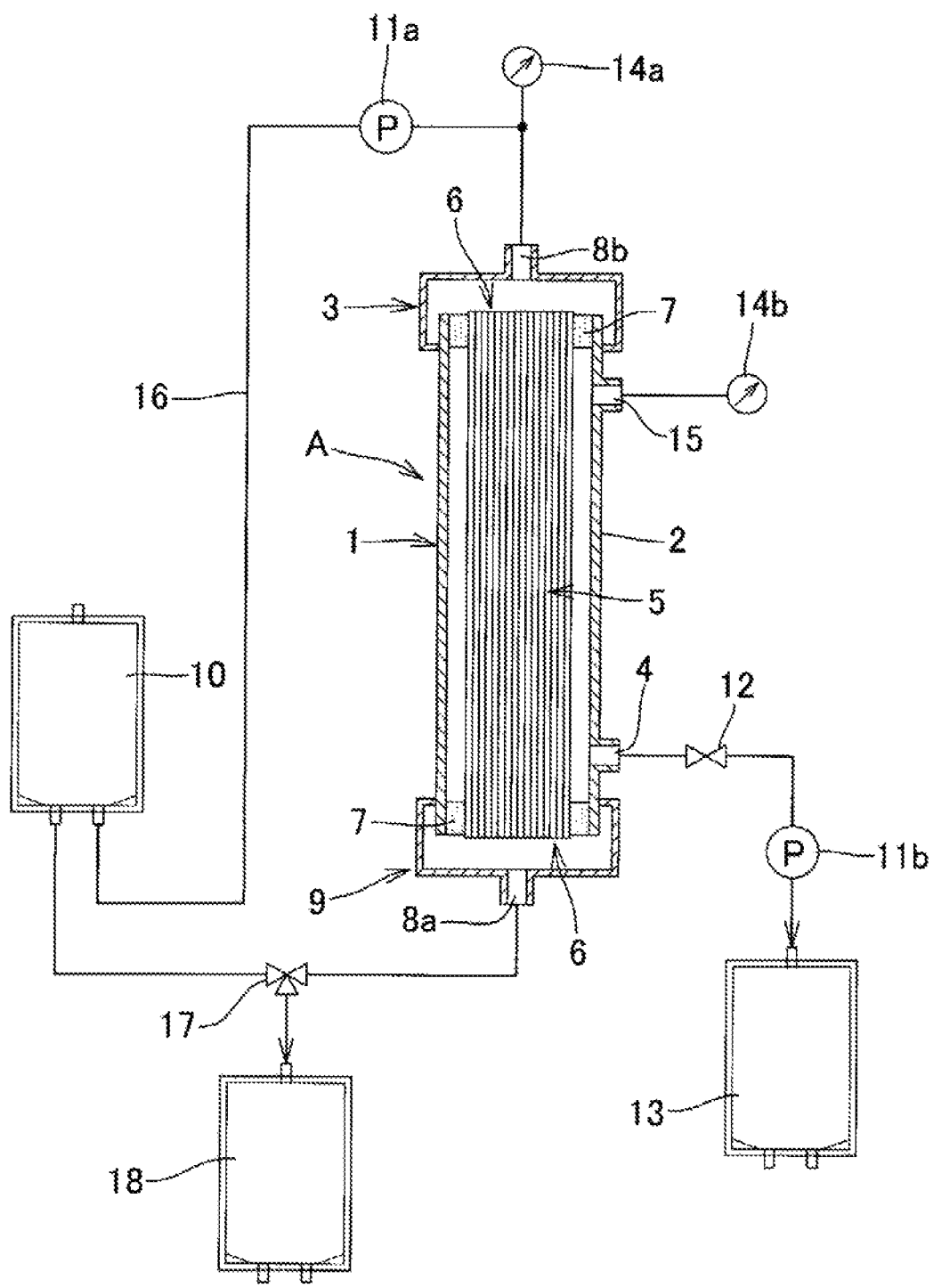
FIG. 1 is a schematic drawing showing an example of the embodiment of the priming method and the production method of a cell concentrate of the present invention.

The hollow-fiber membrane module is not particularly limited as long as it has the configuration described above, and for example, the hollow-fiber membrane module A shown in FIG. 1 can be mentioned. The vessel 1 constituting a hollow-fiber membrane module A includes a body part 2, and a head part 3 and a head part 9 on both sides of the body part 2, and is provided with a filtrate discharge port 4 in the vicinity of the head part 9. As to the position, the filtrate discharge port 4 may be provided in the end part of the head part 9 or of the body part 2, or may be provided in the central part of the body part 2. The number of the filtrate discharge ports 4 is not particularly limited, and considering that the hollow-fiber membrane module is used for separation and filtration applications after priming, it is preferred that one or more filtrate discharge ports 4 are provided, and in order to increase the filtration rate and complete the separation and filtration in a short time, it is more preferred that two filtrate discharge ports 4 and 4' or filtrate discharge ports more than the two filtrate discharge ports 4 and 4' are provided as in the hollow-fiber membrane module B shown in FIG. 2. In addition, it is not required to provide an air release valve in the hollow-fiber membrane module, and the priming can be performed while maintaining a closed system. In the hollow-fiber membrane module B, as to the position, the filtrate discharge port 4 and the filtrate discharge port 4' are provided at substantially the same distance from the inlet port 8a of the hollow-fiber membrane module B, but may be provided at other positions. Further, the filtrate generated in the hollow-fiber membrane module B is introduced into the waste liquid container 13 from the filtrate discharge ports 4 and 4' by driving the pump 11b.

In addition, the hollow-fiber membrane module B has the same configuration as that of the hollow-fiber membrane module A, except that a filtrate discharge port 4' is provided, and a pump 11a' and a pressure gauge 14a' are provided in the circuit 16 on the inlet port 8a side instead of providing the pump 11a and the pressure gauge 14a on the outlet port 8b side. Accordingly, regarding the configuration of the hollow-fiber membrane module B, the description of the configuration common for the hollow-fiber membrane module A will be omitted unless particularly necessary.

Further, in FIG. 1, the inlet port 8a is provided in the lower head part 9, and the outlet port 8b is provided in the upper head part 3. The inlet port 8a is an inlet for introducing a priming liquid into the inside of the hollow fiber membrane, and the outlet port 8b is an outlet through which the priming liquid is derived from the inside of the hollow fiber membrane. Inside the body part 2, a bundle of the loaded hollow fiber membranes 5, a resin layer part 7 fixing the bundle of the loaded hollow fiber membranes 5 to the inside of the body part 2 and further forming the open end 6 of the hollow fiber membranes, which is provided inside the head part 3, and a structure equivalent to this provided inside the head part 9 are included. The resin layer part 7 and the open end 6 have a structure crowned with the head part 3 (or the head part 9), and the inlet port 8a and the outlet port 8b, and the filtrate discharge port 4 are separated by a wall material constituting the hollow fiber membrane, and have a non-continuous structure.

Note that in the hollow-fiber membrane module A shown in FIG. 1, each part is distinguished as the body part 2, the head part 3, and the head part 9 of the vessel 1, but this is for convenience. Even in a case where the body part 2, the head part 3, and the head part 9 of the vessel 1 are formed of separated parts in design, as long as it has a structure in which the inlet port 8a and the outlet port 8b are continuously formed without being separated by a wall material constituting the hollow fiber membrane, and further the inlet port 8a and the outlet port 8b, and the filtrate discharge port 4 are separated by the wall material constituting the hollow fiber membrane, various structures can be used.

The hollow-fiber membrane module A may be sterilized from the viewpoint of preventing contamination of cells with bacteria. The sterilization method is not particularly limited, and a sterilization method widely used for sterilization of medical devices, such as γ ray sterilization, electron beam sterilization, EOG sterilization, and high-pressure steam sterilization can be suitably used.

As the material for the vessel of the hollow-fiber membrane module, an acrylonitrile polymer such as acrylonitrile butadiene styrene terpolymer; a halogenated polymer such as polytetrafluoroethylene, polychlorotrifluoroethylene, a copolymer of tetrafluoroethylene and hexafluoropropylene, and polyvinyl chloride; polyamide, polyimide, polysulfone, polycarbonate, polyethylene, polypropylene, a polyvinyl chloride acrylic copolymer, acrylonitrile, butadiene styrene, polystyrene, polymethylpentene, and the like can be used. In particular, a material having sterilization resistance, specifically, polypropylene, polyvinyl chloride, polyethylene, polyimide, polycarbonate, polysulfone, polymethylpentene, polystyrene, and the like are preferred.

As the material for the resin layer parts for fixing the hollow fiber membranes, a general adhesive material such as a polyurethane resin, an epoxy resin, and a silicone resin can be preferably used.

It is preferred that in the hollow-fiber membrane module, a bundle of around 10 to 1000 hollow fiber membranes is packed in a vessel. In addition, in the present invention, the arrangement of the hollow fiber membranes may be linear, bent, or spiral, and the shape is not particularly limited as long as both ends of the hollow fiber membranes are held between the inlet port and the outlet port. Further, the hollow fiber membranes at the time of priming may be arranged vertically, horizontally or obliquely, but in order to maximize the effective filtration area, it is more preferred that the hollow fiber membranes are arranged in the vertical direction. Note that the effective filtration area refers to the membrane area of the inside of the portion of the hollow fiber membrane of which the outside is immersed in a priming liquid after priming.

A synthetic polymer material can be preferably used for the resin material of the hollow fiber membrane used in the present invention from the viewpoint of the safety, the stability, and the like of the material. Among them, a polysulfone-based or cellulose-based hydrophilic polymer material can be more preferably used. Further, polyethersulfone, and a cellulose ester can be most suitably used from the viewpoint of the safety, the stability, and the availability of the material.

In addition, the lower limit of the pore diameter of the pores provided in the wall of the hollow fiber membrane is preferably 0.07 μm or more, and more preferably 0.1 μm or more. When the pore diameter is 0.07 μm or more, the air existing in the outside of the hollow fiber membrane is easily replaced with the priming liquid during priming, and it is easy for unnecessary contaminants such as proteins to be efficiently removed at the time of the concentration of the cell suspension, which is therefore preferred. When the pore diameter is 0.07 μm or more, the size of the pore is usually expressed by molecular weight cutoff, and for example, in a hollow fiber membrane of around 500 kD, the priming liquid easily passes through the pores of the hollow fiber membrane in spite of surface tension, therefore, the air existing outside of the hollow fiber membrane is easily replaced with the priming liquid. On the other hand, the upper limit of the pore diameter is preferably 1.5 μm or less, more preferably 1.2 μm or less, and further more preferably 1.0 μm or less. Even if the pore diameter exceeds 1.5 μm, there is no particular problem in the priming process. However, when the pore diameter is 1.5 μm or less, the pores having a pore diameter close to the size of the cells are hard to exist on the hollow fiber membrane, therefore, in the process of concentrating a cell suspension, clogging of the pores is hard to be generated, and the cell recovery rate is hard to be largely decreased, which is therefore preferred.

The pore diameter of the pores of the hollow fiber membrane refers to the average pore diameter of the pores of the hollow fiber membrane, and is generally measured and calculated by a perm porometer.

Note that the inner diameter of the inside of the hollow fiber membrane is not particularly limited as long as it has a size through which a cell suspension can pass.

Examples of the priming liquid include physiological saline, distilled water, and an infusion represented by Ringer's solution, a liquid containing inorganic salts, saccharides, serum, and proteins, a buffer, blood plasma, and a medium. Particularly, from the viewpoint of safety, physiological saline, or an infusion can be suitably used. In addition, by coating the surface of the hollow fiber membrane with the proteins, adhesion of the cells to the hollow fiber membrane can be suppressed, and the improvement of the cell recovery rate can be expected, therefore, the liquid containing serum, blood plasma, and proteins can be suitably used as the priming liquid. The priming liquid is not required to be one kind of liquid, and can also be used by mixing two or more liquids from these groups. A combination of physiological saline to which albumin has been added, or a medium to which serum has been added can be mentioned as an example of using two or more liquids as a mixture thereof.

The priming method of the present invention is characterized by including a priming process in which before the introduction of a cell suspension, a priming liquid is filled in a hollow-fiber membrane module in an amount of 15% or more relative to the volume of the hollow-fiber membrane module at a linear velocity of 20 cm/min or more and 550 cm/min or less, preferably at a linear velocity of 35 cm/min or more and 450 cm/min or less, and more preferably at a linear velocity of 35 cm/min or more and 300 cm/min or less from the inlet port or the outlet port of the hollow-fiber membrane module. In this way, the effective filtration area of the hollow-fiber membrane module at the time of cell treatment is enlarged, and the filtration rate can be improved without causing lowering of the cell recovery rate.

Note that the effective filtration area refers to the membrane area of the inside of the portion of the hollow fiber membrane of which the outside is immersed in a priming liquid, and in the present invention, can be determined by the following Equation 1:

(effective filtration area($cm^2$))=π×(hollow fiber inner diameter(cm))×(length of portion of hollow fiber membrane of which the outside is immersed in priming liquid(cm))×(the number of hollow fibers(fibers))     (Equation 1).

The linear velocity (cm/min) refers to the amount of the liquid flowing into the inside of the hollow fiber membrane per unit of time, that is, is a value obtained by dividing the flow rate ($cm^3$/min=mL/min) by the total cross-sectional area of hollow fiber membrane ($cm^2$).

In the priming method of the present invention, the lower limit of the linear velocity of the priming liquid to be introduced into the inside of the hollow fiber membrane is 20 cm/min, and is preferably 35 cm/min from the viewpoint of the shortening and the efficiency of the priming process. Further, the upper limit of the linear velocity of the priming liquid to be introduced into the inside of the hollow fiber membrane is 550 cm/min, preferably 450 cm/min, more preferably 420 cm/min, and further more preferably 300 cm/min. When the linear velocity is less than 20 cm/min, there is a concern that the priming process takes an extremely long time, and when the linear velocity exceeds 550 cm/min, the inside of the hollow fiber membrane is infiltrated by a priming liquid before the air in the outside of the hollow fiber membrane is replaced with the priming liquid, and the outside of the hollow fiber membrane cannot be filled with the priming liquid.

Note that the total cross-sectional area of the hollow fiber membrane referred to herein is the total area of the cross-sectional areas of the inside of the hollow fiber membranes packed in the hollow-fiber membrane module, and can be determined by the following Equation 2:

(total cross-sectional area($cm^2$))=(the number of hollow fibers (fibers))×π×(hollow fiber inner diameter(cm))×(hollow fiber inner diameter(cm))÷4     (Equation 2).

Alternatively, the total cross-sectional area can be determined from the hollow fiber inner diameter (cm), the filtration area ($cm^2$), and the distance (cm) between the resin layer parts, by the following Equation 3:

(total cross-sectional area($cm^2$))=[(hollow fiber inner diameter(cm)]×[filtration area($cm^2$)]÷[distance between resin layer parts(cm)]÷4     (Equation 3).

Further, the filtration area is a value determined by the following Equation 4:

(filtration area($cm^2$))=π×(hollow fiber inner diameter (cm))×(distance between resin layer parts(cm))× (the number of hollow fibers(fibers))     (Equation 4).

The distance between the resin layer parts refers to the distance between the resin layer parts between which hollow fibers have been fixed at two positions of the upper and lower portions in the hollow-fiber membrane module.

The volume ($cm^3$) of the hollow-fiber membrane module can be calculated by the following Equation 5:

(volume of hollow-fiber membrane module($cm^3$))= (total cross-sectional area of hollow-fiber membrane module($cm^2$))×(distance between resin layer parts at both ends of hollow-fiber membrane module(cm))     (Equation 5).

The volume of the hollow-fiber membrane module is preferably 10 $cm^3$ or more and 500 $cm^3$ or less. When the volume is less than 10 $cm^3$, the distance between the resin layer parts at both ends of the hollow-fiber membrane module cannot be sufficiently secured, and in that case, even when the priming treatment of the present invention is performed, the inside of the hollow fiber membrane is immediately thoroughly wet, and the air outside the hollow fiber membrane is not replaced with the priming liquid. Further, when the volume exceeds 500 $cm^3$, there is a concern that the priming process takes an extremely long time. The lower limit of the volume is more preferably 20 $cm^3$, and further more preferably 30 $cm^3$. The upper limit of the volume is more preferably 400 $cm^3$, and further more preferably 300 $cm^3$.

In the priming method of the present invention, the priming liquid is filled in a vessel constituting the hollow-fiber membrane module to an amount of 15% or more relative to the volume of the vessel. Herein, the filling rate of the priming liquid refers to the amount filled in the vessel after priming, and specifically, the filling rate (%) of the priming liquid can be calculated by displaying in percent the value obtained by dividing the length (cm) of the portion of the hollow fiber membrane of which the outside is immersed in the priming liquid by the distance (cm) between the resin layer parts at both ends of the hollow-fiber membrane module.

When the filling rate of the priming liquid is less than 15%, the effective filtration area is small, therefore, when the liquid containing cells is treated, the cells easily clog the hollow fiber membrane, and it is concerned that lowering of the cell recovery rate is caused. The filling rate of the priming liquid is preferably 40% or more, and when the filling rate is 70% or more, the cells do not easily clog the hollow fiber membrane, and as a result the cell recovery rate becomes higher, which is therefore more preferred.

In addition, in the priming method of the present invention, it is preferred that the pressure difference between the internal pressure and the external pressure at the time of priming is adjusted to be 7 mmHg (933 Pa) or more and 29 mmHg (3866 Pa) or less.

The internal pressure (mmHg or Pa) of the hollow fiber membrane is an absolute value of the pressure of the inside of the hollow fiber membrane at the time of priming, and makes reference to the absolute value of the pressure measurement value of the air in the vicinity of the inlet/outlet port (outlet port and/or inlet port) of the hollow-fiber membrane module. Therefore, in a case of arranging a pump in the vicinity of the inlet port of a priming liquid to control the linear velocity and introducing the priming liquid into the inside of the hollow fiber membrane, the internal pressure measurement value (also referred to as internal pressure value) becomes positive pressure, and conversely in a case of arranging a pump in the vicinity of the outlet port of a priming liquid to control the linear velocity and introducing the priming liquid into the inside of the hollow fiber membrane, the internal pressure value becomes negative pressure. The internal pressure value is preferably negative pressure. When the internal pressure value becomes negative pressure, the introduction of the priming liquid into the inside of the hollow fiber membrane and the replacement of the air in the outside of the hollow fiber membrane with the priming liquid can be performed more efficiently.

For example, in the hollow-fiber membrane module A shown in FIG. 1, the linear velocity is controlled by using the pump 11a provided in the vicinity of the outlet port 8b of the priming liquid, therefore, the internal pressure becomes negative pressure. As described above, when the internal pressure becomes negative pressure, the introduction of the priming liquid into the inside of the hollow fiber membrane and the replacement of the air in the outside of the hollow fiber membrane with the priming liquid can be performed more efficiently. The lower limit of the internal pressure is preferably 8 mmHg (1067 Pa), and the upper limit of the internal pressure is preferably 66 mmHg (8799 Pa).

Figure 2:
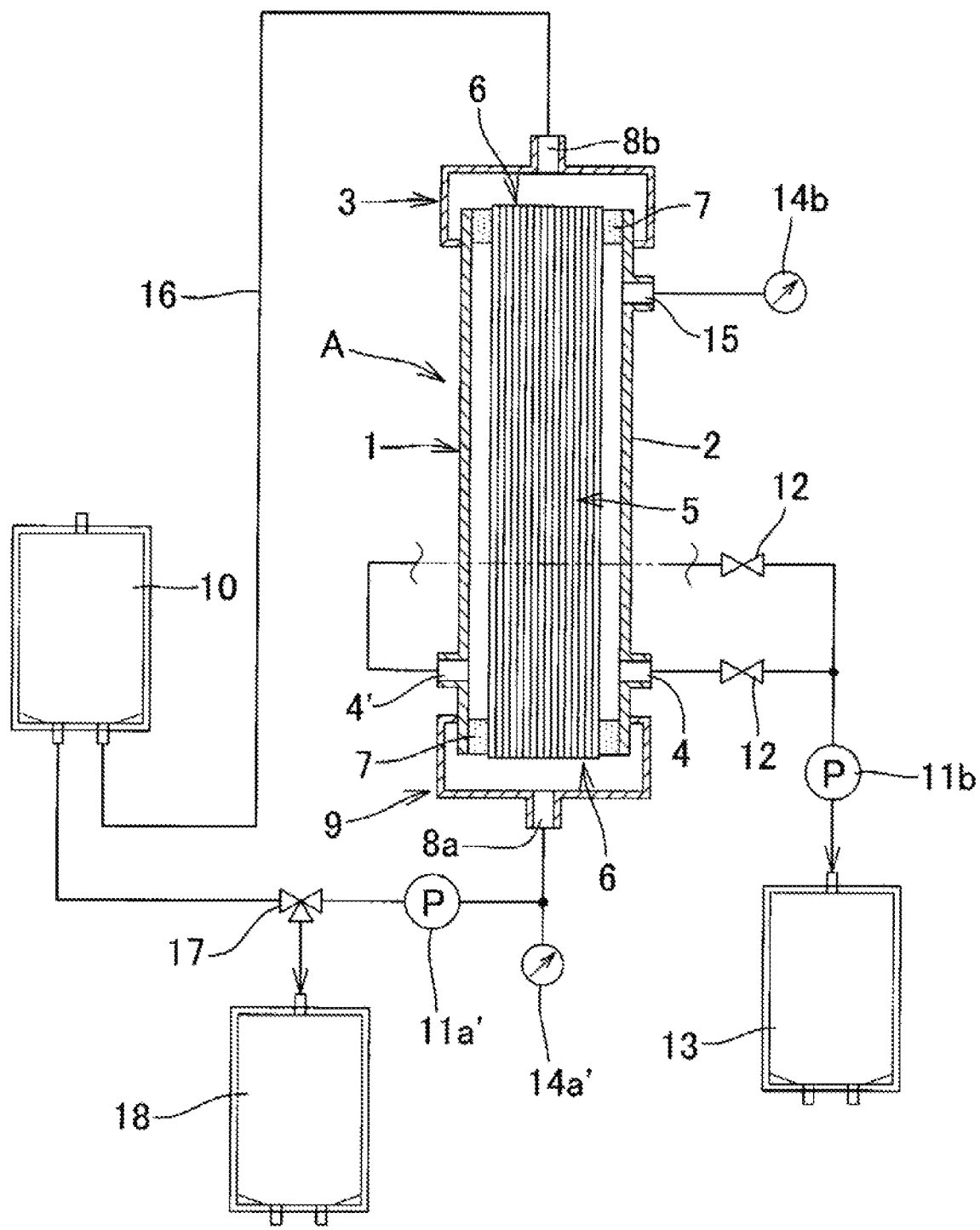
FIG. 2 is a schematic drawing showing another example of the embodiment of the priming method and the production method of a cell concentrate of the present invention.

Further, as in the hollow-fiber membrane module B shown in FIG. 2, in a case where a pump 11a' is provided in the vicinity of the inlet port 8a of a priming liquid, the linear velocity of the priming liquid to be introduced into the hollow-fiber membrane module B is controlled by using the pump 11a', therefore, the internal pressure becomes positive pressure.

In addition, as to the method for measuring the internal pressure, the pressure of the liquid introduced into the inside of the hollow fiber membrane 5 packed in the hollow-fiber membrane module A may be measured. For example, as shown in FIG. 1, the internal pressure may be measured by connecting a pressure gauge 14a to an arbitrary position of the tube connecting the outlet port 8b of a priming liquid and the pump 11a, or as shown in FIG. 2, a pressure gauge 14a' for measuring the internal pressure may be connected to an arbitrary position of the tube connecting the inlet port 8a of a priming liquid and the pump 11a'.

Further, the external pressure (mmHg or Pa) of the hollow fiber membrane is an absolute value of the pressure of the outside of the hollow fiber membrane at the time of priming, and makes reference to the absolute value of the pressure measurement value of the air in the space outside the hollow fiber membrane. In a case of arranging a pump in the vicinity of the inlet port of a priming liquid to control the linear velocity and introducing the priming liquid into the inside of the hollow fiber membrane, the external pressure measurement value (also referred to as external pressure value) becomes positive pressure, and conversely in a case of arranging a pump in the vicinity of the outlet port of a priming liquid to control the linear velocity and introducing the priming liquid into the inside of the hollow fiber membrane, the external pressure value becomes negative pressure. It is preferred that the lower limit of the external pressure is 0 mmHg (0 Pa), and the upper limit of the external pressure is 46 mmHg (6133 Pa).

In addition, as to the method for measuring the external pressure, the pressure of the liquid in the space of the hollow fiber membranes 5 packed in the hollow-fiber membrane module A or B shown in FIG. 1 or 2 and the body part 2 may be measured, and for example, in FIG. 1, a pressure gauge connection port 15 is provided in the side of the body part 2, and the external pressure may be measured by connecting a pressure gauge 14b to the pressure gauge connection port 15.

The pressure difference (mmHg or Pa) refers to an absolute value of the difference obtained by subtracting the external pressure measurement value from the internal pressure measurement value.

In a case where the pressure difference is 7 mmHg (933 Pa) or more, the linear velocity is not extremely low and the priming process does not take a long time. Further, when the pressure difference is 29 mmHg (3866 Pa) or less, the linear velocity is not extremely high and the inside of the hollow fiber membrane is not immediately thoroughly wet with the priming liquid, and the air in the outside of the hollow fiber membrane is easily replaced with the priming liquid.

In the priming method of the present invention, the lower limit of the pressure difference is preferably 7 mmHg (933 Pa), and the upper limit of the pressure difference is preferably 29 mmHg (3866 Pa), more preferably 22 mmHg (2933 Pa), and further more preferably 17 mmHg (2266 Pa).

Further, in a case of controlling the linear velocity by using a pump provided in the vicinity of the inlet port of a priming liquid and introducing the priming liquid into the inside of the hollow fiber membrane from the inlet port, the difference obtained by subtracting the external pressure value from the internal pressure value becomes a positive value, and conversely in a case of controlling the linear velocity by using a pump provided in the vicinity of the outlet port of a priming liquid and introducing the priming liquid into the inside of the hollow fiber membrane from the inlet port, the difference obtained by subtracting the external pressure value from the internal pressure value becomes a negative value.

In addition, the present invention relates to a method for producing a cell concentrate including, after applying the priming method as described above to the hollow-fiber membrane module, introducing a cell suspension into the hollow-fiber membrane module from the inlet port or the outlet port of the hollow-fiber membrane module, and concentrating the cell suspension while discharging a filtrate containing no cells from the filtrate discharge port.

Examples of the cells in this case include living pluripotent stem cells such as induced pluripotent stem cells (iPS cells), embryonic stem cells (ES cells), mesenchymal stem cells, adipose-derived mesenchymal cells, adipose-derived stromal stem cells, pluripotent adult stem cells, bone marrow stromal cells, and hematopoietic stem cells, lymphoid cells such as T cells, B cells, killer T cells (cytotoxic T cells), NK cells, NKT cells, and regulatory T cells, macrophages, monocytes, dendritic cells, granulocytes, red blood cells, platelets, somatic cells such as nerve cells, muscle cells, fibroblasts, liver cells, and myocardial cells, cells subjected to a treatment such as gene transfer, and differentiation, tumor cells, endothelial cells, and rare cells such as fetal cells.

The cell suspension is not particularly limited as long as it is a suspension containing the cells, and examples of the cell suspension include a suspension obtained by subjecting living tissues of fat, skin, blood vessels, cornea, oral cavity, kidney, liver, pancreas, heart, nerve, muscle, prostate, intestines, amnion, placenta, umbilical cord, or the like to a treatment such as enzymatic treatment, crushing treatment, extraction treatment, decomposition treatment, or ultrasonic treatment; and a cell suspension prepared by subjecting blood or bone marrow aspirate to a pretreatment such as density gradient centrifugation treatment, filtration treatment, enzymatic treatment, decomposition treatment, or ultrasonic treatment.

Further, a cell suspension obtained by culturing the cells mentioned above in vitro may be used. Examples of the culture medium when cells are cultured in vitro include DMEM, α-MEM, MEM, IMEM, and RPMI-1640. Furthermore, as the culture medium, a culture medium in which stimulating factors such as cytokines, antibodies, or peptides have been added may also be used.

The process of concentrating the cell suspension is specifically a process in which components such as proteins and inorganic salts, which contain no cells, are filtered to the outside of the hollow fiber membrane as a filtrate from the cell suspension that has flowed inside the hollow fiber membrane from the inlet port or outlet port of the hollow-fiber membrane module, and the cell suspension in which cell components have been concentrated is flown out from the inlet port or the outlet port. In addition, the inlet port and the outlet port of the hollow-fiber membrane module are connected by a circuit, and configured so as to make the concentrated cell concentrate flow inside the hollow fiber membrane again and further concentrate the cell components. By repeating this concentration, the concentration of the cell suspension progresses, and a cell concentrate that has been concentrated to the desired cell concentration is generated. Note that the cell concentrate refers to a cell suspension concentrated by passing through the hollow-fiber membrane module.

The cell suspension may also be introduced into the hollow-fiber membrane module from the inlet port in the same manner as a priming liquid, or conversely may also be introduced into the hollow-fiber membrane module from the outlet port of the priming liquid.

It is preferred that the linear velocity of the cell suspension when the cell suspension is introduced into the hollow-fiber membrane module is larger than 500 cm/min and 2000 cm/min or less.

When the linear velocity is 500 cm/min or less, the concentration treatment takes a long time, and this is not efficient. When the linear velocity exceeds 2000 cm/min, there is a concern that the damage due to the shearing or pressure to the cells is increased.

The lower limit of the linear velocity is preferably higher than 500 cm/min, more preferably higher than 800 cm/min, and further more preferably higher than 1200 cm/min. Further, the upper limit of the linear velocity is preferably 2000 cm/min, more preferably 1800 cm/min, and further more preferably 1500 cm/min.

The filtration rate ($mL/m^2/min$) of the cell suspension in the concentration process is preferably 1000 $mL/m^2/min$ or more and 4250 $mL/m^2/min$ or less.

The filtration rate is a value obtained by dividing the flow rate ($mL/m^2$) per 1 $m^2$ of the hollow fiber membrane area of the filtrate discharged from the filtrate discharge port by the time (min).

When the filtration rate is less than 1000 $mL/m^2/min$, the concentration treatment takes a long time, and this is not efficient. When the linear velocity exceeds 4250 $mL/m^2/min$, the cells easily clog the hollow fiber membrane, and there is a concern that the lowering of the cell recovery rate is caused.

In addition, the lower limit of the filtration rate is preferably 1000 $mL/m^2/min$, more preferably 1250 $mL/m^2/min$, and more preferably 1500 $mL/m^2/min$. Further, the upper limit of the filtration rate is preferably 4250 $mL/m^2/min$, more preferably 4000 $mL/m^2/min$, and more preferably 3750 $mL/m^2/min$.

Among them, when the filtration rate of the cell suspension is 1500 $mL/m^2/min$ or more and 3750 $mL/m^2/min$ or less, the concentration treatment can be realized in a short time and with high recovery efficiency, which is therefore preferred.

Note that the hollow fiber membrane area when the filtration rate is determined refers to the membrane area of the whole hollow fiber membranes packed in the hollow-fiber membrane module, regardless of whether or not the outside of the hollow fiber membrane is infiltrated with a liquid, and is calculated by (membrane area ($m^2$))=(hollow fiber inner diameter (m))×π×(distance between resin layer parts (m))×(the number of hollow fibers (fibers)).

As the membrane area, 0.05 $m^2$ or more and 0.20 $m^2$ or less is preferred. When the membrane area exceeds 0.20 $m^2$, there is a concern that the amount of the cell suspension left in the hollow fiber membrane is increased, and the recovery rate is lowered, and when the membrane area is less than 0.05 $m^2$, the filtration flow rate is not sufficient and the treatment cannot be performed in a short time, or the cells easily clog the hollow fiber membrane, and there is a concern that the lowering of the cell recovery rate is caused. The lower limit of the membrane area is preferably 0.05 $m^2$, more preferably 0.07 $m^2$, and further more preferably 0.09 $m^2$. The upper limit of the membrane area is preferably 0.20 $m^2$, more preferably 0.18 $m^2$, and further more preferably 0.16 $m^2$.

Hereinafter, the priming method and the method for producing a cell concentrate of the present invention will be mentioned by using FIG. 1, however, the present invention is not limited to the methods, and various changes can be performed in the range where the gist of the present invention is not impaired.

At first, tubes and the like are attached to an inlet port 8a and an outlet port 8b of a hollow-fiber membrane module A. Both ends of the tubes attached to the inlet port 8a and the outlet port 8b are connected to a storage container 10 such as a bag containing a priming liquid, and a circuit 16 is formed so that a liquid such as a priming liquid circulates between the storage container 10 and the hollow-fiber membrane module A. Further, a pump 11a may be interposed in the tube so that a liquid such as a priming liquid circulates in the attached tubes. In addition, the filtrate discharge port 4 is kept in a state of being closed with a straight stopcock 12 until the priming process is completed. The entire assembly of the hollow-fiber membrane module A, the tubes, and the like is preferably performed under an aseptic environment such as in a clean bench.

Next, a priming liquid is filled into the inside of hollow fiber membrane from the inlet port 8a positioned in the lower part of the hollow-fiber membrane module A by moving the pump 11a counterclockwise as viewed from the circuit 16 shown in FIG. 1. The driving speed of the pump 11a is adjusted so that the linear velocity of the priming liquid is 20 cm/min or more and 550 cm/min or less, preferably 35 cm/min or more and 450 cm/min or less, and more preferably 35 cm/min or more and 300 cm/min or less, and the pump 11a is stopped after confirmation that the priming liquid has been filled in the hollow-fiber membrane module A in an amount of 15% or more relative to the volume of the hollow-fiber membrane module A, and the priming is ended.

Next, when the priming has been completed, the priming liquid in the storage container 10 is replaced with a cell suspension, a straight stopcock 12 in the tube connecting a filtrate discharge port 4 and a waste liquid container 13 is opened, and the process of concentrating the cell suspension is started by moving the pump 11a counterclockwise as viewed from the circuit 16 shown in FIG. 1.

At this time, the filtration can also be performed while applying pressure to the hollow fiber membranes for example, by narrowing the flow path in the filtrate discharge port 4 side, the filtration may also be performed while applying pressure by arranging a machine 11b such as a pump in the tube in the filtration side, or various filtration methods used in a general hollow fiber membrane module may be used in combination.

In addition, as a method for recovering the cell concentrate after the concentration process, for example, a method in which a three-way stopcock 17 is provided as a branch part in an appropriate place of the circuit 16 connecting the inlet port 8a and the storage container 10, a recovery container 18 is connected to the three-way stopcock 17 in the branch part, and the cell concentrate in the hollow-fiber membrane module A, the storage container 10, and the circuit 16 is introduced into the recovery container 18 while driving the pump 11a can be mentioned, but there is no particular limitation.

As described above, since there is no contamination of bacteria and the like in the cell concentrate obtained by maintaining the closed environment, the cell concentrate can be directly provided as it is to the therapeutic applications for various kinds of diseases.

For example, the method is related to a therapeutic method for various kinds of diseases, in which the cell concentrate obtained by the above-described production method is administered to a human or a non-human animal.

Examples of the therapeutic method include immune cell therapy for cancer, using immune cells such as cytotoxic T cells, NK cells, NKT cells, and dendritic cells; cell transplantation therapy for tissue regeneration of bones, joints, blood vessels, organs, and the like, using living pluripotent stem cells such as mesenchymal stem cells; and GVHD therapy using mesenchymal stem cells. Cells derived from iPS cells or ES cells, or cells to which various kinds of genes have been introduced may also be used as the cells used in these therapies. In addition, the cell concentrate obtained in the above-described production method can be suitably used also as an application of culture medium exchange for adding a fresh medium to the cell concentrate and performing the culture again.

EXAMPLES

Hereinafter, the present invention will be described with reference to experimental results.

The cell recovery rate (%) is a value obtained by dividing the number of the cells in the cell suspension at the time point when the concentration becomes a certain amount by the number of the cells in the cell suspension before the treatment, and it is indicated that the higher the value is, the more excellent the recovery efficiency is.

The number of cells (cells) can be calculated by measuring the cell suspension with a blood cell counter (trade name "K-4500", manufactured by SYSMEX CORPORATION) and calculating the cell concentration of the leukocyte fraction as the cell concentration in the present Example, and by the product of the cell suspension volume (mL) and the cell concentration (cells/mL).

The cell recovery rate (%) is preferably 70% or more, and more preferably 85% or more. When the cell recovery rate is less than 85%, there may be a case where the required number of cells cannot be secured at the time of administering the cells to a patient as the cell therapy application. When the cell recovery rate is less than 70%, it may be determined to be unsuitable for use as the cell treatment application because cell loss is extremely large.

In addition, herein the cell survival rate ratio is a value displayed in percentage, which is obtained by dividing the cell survival rate in the cell suspension recovered in the recovery container 18 by the cell survival rate in the cell suspension before the treatment, and it is indicated that the higher the value is, the less the damage to the cells is. The cell survival rate is calculated from the equation of {cell survival rate (%)=100−dead cell rate (%)}.

The dead cell rate (%) can be measured as a positive rate (%) of via-probe by adding 10 μL of via-probe (manufactured by Becton, Dickinson and Company) to 100 μL of each cell suspension that has been prepared so that the cell concentration is the sixth power of 10 per 1 mL, leaving the resultant mixture to stand at room temperature in a dark place for 10 minutes, and then taking it to a flow cytometer ("FACSCanto" manufactured by Becton, Dickinson and Company).

In the present invention, the cell survival rate ratio is preferably 95% or more, and more preferably 96% or more. When the cell survival rate is less than 95%, the cells have been largely damaged in the cell concentration process, therefore, for example, when the resultant product is administered to a patient as the cell therapy application, there may be a case where the cells do not function normally, and do not exert any therapeutic effects.

As the cell suspension to be used in Examples, 1500 mL of a cell suspension containing cultured Jurkat cells (10% FBS-containing RPMI 1640 medium) was used.

The priming method and the method for producing a cell concentrate in each experimental example were performed by using an apparatus in which a hollow-fiber membrane module A, a storage container 10, and a waste liquid container 13 are connected by tubes as shown in FIG. 1. As the hollow-fiber membrane module A, a hollow-fiber membrane module A in which an inlet port 8a is provided to the bottom of a head part 9 positioned in the lower part of the hollow-fiber membrane module A, and a filtrate discharge port 4 is provided in the side of a body part 2 in the vicinity of the inlet port 8a, and the outlet port 8b is provided to the top of a head part 3 positioned in the upper part of the hollow-fiber membrane module A, and a pressure gauge connection port 15 is provided in the side of the body part 2 in the vicinity of the outlet port 8b was used.

In addition, a vinyl chloride tube was connected to each of the inlet port 8a and the outlet port 8b of the hollow-fiber membrane module A described in each Example. Both of the other ends of the vinyl chloride tubes connected to the inlet port 8a and the outlet port 8b, were respectively connected to the storage container 10 made of plastic in which physiological saline is stored, and a circuit 16 was formed so that the physiological saline in the storage container 10 circulates between the hollow-fiber membrane module A and the storage container 10 via the tubes.

A pump 11a and an internal pressure gauge 14a were arranged in the vinyl chloride tube in the outlet port 8b side, and the flow rate was set so that the physiological saline flows at the flow rate described in Examples below.

A tube and a straight stopcock 12 were attached to the filtrate discharge port 4 of the hollow-fiber membrane module A, the end of the tube was connected to the waste liquid container 13, further a pump 11b was arranged in the tube, the flow rate was set so that the filtrate is discharged at the flow rate described in Examples below, and the straight stopcock 12 was closed.

In addition, an external pressure gauge 14b was attached to the pressure gauge connection port 15.

Further, a three-way stopcock 17 was attached to the tube connected to the storage container 10 and the inlet port 8a of the hollow-fiber membrane module A, and moreover, a recovery container 18 made of plastic was connected to the three-way stopcock 17 via a tube.

Next, by driving the pump 11a, physiological saline was filled in the hollow-fiber membrane module A from the inlet port 8a, and at this time, each value (mmHg) of the external pressure gauge 14b and the internal pressure gauge 14a, and the length (cm) of the portion of the hollow fiber membrane of which the outside was immersed in a priming liquid were recorded, respectively.

Note that the value of the external pressure gauge 14b was set as the "external pressure" of the hollow fiber membrane, and the value of the internal pressure gauge 14a was set as the "internal pressure" of the hollow fiber membrane.

Further, the filling efficiency (%) of the priming liquid was calculated by displaying in percent the value obtained by dividing the length (cm) of the portion of the hollow fiber membrane of which the outside was immersed in a priming liquid by the distance (cm) between the resin layer parts at both ends of the hollow-fiber membrane module.

Subsequently, the straight stopcock 12 was opened, the storage container 10 in which physiological saline was stored was replaced with another storage container 10 in which a cell suspension was stored, the flow rate of the pump 11a was set so as to be the flow rate described in Examples below, and the flow direction was set so as to be the direction opposite to the flow direction of the priming liquid.

That is, a cell suspension was introduced from the outlet port 8b into the hollow-fiber membrane module A, and a filtrate was discharged from the filtrate discharge port 4 while circulating the cell suspension between the hollow-fiber membrane module A and the storage container 10.

After the concentration was performed until the volume of the filtrate became a certain volume (70 to 80 mL), the straight stopcock 12 was closed, the cell concentrate in the tube and the hollow fiber separation membranes 5 was extruded from the inlet port 8a at a flow rate of 75 mL/min by the pump 11a, and recovered in the recovery container 18 branched from the circuit 16 positioned between the inlet port 8a and the storage container 10.

The time required from the start of the flow of the cell suspension to the end of the recovery was measured by a stopwatch to determine the treatment time. In the end, the number of the cells of the cell concentrate in the recovery container 18 was measured, and the cell recovery rate and the survival rate ratio were calculated. Hereinafter, Examples will be shown.

Example 1

300 hollow fiber membranes made of polyethersulfone (PES) [trade name: MFC-K1, with a hollow fiber inner diameter of 570 μm, and a pore diameter of 0.2 μm, manufactured by TOYOBO CO., LTD.] were packed in a cylindrical vessel 1 having a diameter of 4.5 cm and a height of 24 cm provided with a filtrate discharge port 4 and a pressure gauge connection port 15 in the side end part of the cylindrical vessel 1, and both ends of a bundle of the hollow fiber membranes 5 were fixed to the inside of the vessel 1 by the resin layer parts 7.

The distance between the resin layer parts 7 at both ends at this time was 23 cm. Next, the head parts (3 and 9) provided with an inlet port 8a and an outlet port 8b respectively were attached to both end faces of the cylindrical vessel 1 respectively to obtain a hollow-fiber membrane module A.

The filtration area of the prepared hollow-fiber membrane module A was calculated to be 0.18 m$^2$, and the total cross-sectional area was calculated to be 0.77 cm$^2$ by using the Equation 2 described above. As the priming condition, the flow rate at the outlet port was set to 27 mL/min (linear velocity of 35 cm/min).

At this time, the internal pressure value was −8 mmHg, the external pressure value was −1 mmHg, and the absolute value of the pressure difference was 7 mmHg.

Further, the distance between the resin layer parts 7 at both ends of the hollow-fiber membrane module A was 23 cm, and the length in the vertical direction of the hollow fiber membrane of which the outside was immersed in a priming liquid at the end of priming was 21 cm.

Therefore, the filling efficiency of the priming liquid (ratio of the length of the hollow fiber membrane of which the outside was immersed in a priming liquid to the distance between the resin layer parts 7 at both ends of the module) was calculated to be 91%.

As the concentration condition, the flow rate in the vicinity of the outlet port 8b of the priming liquid was set to 450 mL/min (linear velocity of 588 cm/min), and the filtration rate discharged from the filtrate discharge port 4 was set to 1823 mL/m$^2$/min. As a result, the treatment time was 362 seconds, the cell recovery rate was 86%, and the survival rate ratio was 97%.

Example 2

A hollow-fiber membrane module A similar to that in Example 1 was used. As the priming condition, the flow rate in the vicinity of the outlet port 8*b* was set to 230 mL/min (linear velocity of 300 cm/min).

At this time, the internal pressure value was −32 mmHg, the external pressure value was −15 mmHg, and the pressure difference was 17 mmHg.

Further, the distance between the resin layer parts 7 at both ends of the hollow-fiber membrane module A was 23 cm, and the length of the hollow fiber membrane of which the outside was immersed in a priming liquid was 17 cm.

Therefore, the filling efficiency of the priming liquid was calculated to be 74%.

As the concentration condition, the flow rate in the vicinity of the outlet port 8*b* of the priming liquid was set to 450 mL/min (linear velocity of 588 cm/min), and the filtration rate discharged from the filtrate discharge port 4 was set to 1823 mL/m$^2$/min. As a result, the treatment time was 364 seconds, the cell recovery rate was 85%, and the survival rate ratio was 96%.

Example 3

A hollow-fiber membrane module A similar to that in Example 1 was used. As the priming condition, the flow rate in the vicinity of the outlet port 8*b* was set to 322 mL/min (linear velocity of 420 cm/min). At this time, the internal pressure value was −34 mmHg, the external pressure value was −12 mmHg, and the pressure difference was 22 mmHg.

Further, the distance between the resin layer parts 7 at both ends of the hollow-fiber membrane module A was 23 cm, and the length of the hollow fiber membrane of which the outside was immersed in a priming liquid was 10 cm.

Therefore, the filling efficiency of the priming liquid was calculated to be 44%.

As the concentration condition, the flow rate in the vicinity of the outlet port 8*b* of the priming liquid was set to 450 mL/min (linear velocity of 588 cm/min), and the filtration rate discharged from the filtrate discharge port 4 was set to 1823 mL/m$^2$/min. As a result, the treatment time was 365 seconds, the cell recovery rate was 73%, and the survival rate ratio was 97%.

Example 4

A hollow-fiber membrane module A similar to that in Example 1 was used. As the priming condition, the flow rate in the vicinity of the outlet port 8*b* was set to 344 mL/min (linear velocity of 450 cm/min). At this time, the internal pressure value was −36 mmHg, the external pressure value was −7 mmHg, and the pressure difference was 29 mmHg.

Further, the distance between the resin layer parts 7 at both ends of the hollow-fiber membrane module A was 23 cm, and the length of the hollow fiber membrane of which the outside was immersed in a priming liquid was 4 cm.

Therefore, the filling efficiency of the priming liquid was calculated to be 17%.

As the concentration condition, the flow rate in the vicinity of the outlet port 8*b* of the priming liquid was set to 450 mL/min (linear velocity of 588 cm/min), and the filtration rate discharged from the filtrate discharge port 4 was set to 1823 mL/m$^2$/min. As a result, the treatment time was 363 seconds, the cell recovery rate was 70%, and the survival rate ratio was 95%.

Example 5

By using a hollow-fiber membrane module A similar to that in Example 1, priming was performed under the same conditions as those in Example 1.

As the concentration condition, the flow rate in the vicinity of the outlet port 8*b* of the priming liquid was set to 600 mL/min (linear velocity of 784 cm/min), and the filtration rate discharged from the filtrate discharge port 4 was set to 2422 mL/m$^2$/min.

As a result, the treatment time was 297 seconds, the cell recovery rate was 76%, and the survival rate ratio was 98%.

Example 6

A hollow-fiber membrane module A in which hollow fiber membranes made of mixed cellulose ester (ME) [trade name: D06-M20U-06-N, with a hollow fiber inner diameter of 600 µm, and a pore diameter of 0.2 µm, manufactured by Spectrum Laboratories Inc.] was packed in a cylindrical vessel 1 having a diameter of 6.98 mm and a height of 68 cm provided with a filtrate discharge port 4 and a pressure gauge connection port 15 in the side end part of the cylindrical vessel 1 so that the filtration area is 335 cm$^2$, and both ends of the hollow fiber membranes were fixed by the resin layer parts 7 was used.

The distance between the resin layer parts 7 at both ends at this time was 65 cm. By substituting these values in the Equation 3, the total cross-sectional area of the hollow fiber membranes was calculated to be 0.077 cm$^2$.

As the priming condition, the flow rate in the vicinity of the outlet port 8*b* was set to 2.7 mL/min (linear velocity of 35 cm/min). At this time, the internal pressure value was −55 mmHg, the external pressure value was −46 mmHg, and the pressure difference was 9 mmHg. Further, the distance between the resin layer parts 7 at both ends of the hollow-fiber membrane module A was 65 cm, and the length in the vertical direction of the hollow fiber membrane of which the outside was immersed in a priming liquid was 62 cm.

Therefore, the filling efficiency of the priming liquid was calculated to be 95%.

Example 7

A hollow-fiber membrane module A in which hollow fiber membranes made of mixed cellulose ester (ME) [trade name: D06-M10U-06-N, with a hollow fiber inner diameter of 600 µm, and a pore diameter of 0.1 µm, manufactured by Spectrum Laboratories Inc.] was packed in a cylindrical vessel 1 having a diameter of 6.98 mm and a height of 68 cm provided with a filtrate discharge port 4 and a pressure gauge connection port 15 in the side end part of the cylindrical vessel 1 so that the filtration area is 335 cm$^2$, and both ends of a bundle of the hollow fiber membranes 5 were fixed to the inside of the vessel 1 by the resin layer parts 7 was used.

The distance between the resin layer parts 7 at both ends at this time was 65 cm. By substituting these values in the Equation 3, the total cross-sectional area of the hollow fiber membranes was calculated to be 0.077 cm$^2$.

As the priming condition, the flow rate in the vicinity of the outlet port 8*b* was set to 2.7 mL/min (linear velocity of 35 cm/min). At this time, the internal pressure value was −66 mmHg, the external pressure value was −46 mmHg, and the pressure difference was 20 mmHg. Further, the distance between the resin layer parts 7 at both ends of the hollow-fiber membrane module was 65 cm, and the length of the hollow fiber membrane of which the outside was immersed in a priming liquid was 46 cm.

Therefore, the filling efficiency of the priming liquid was calculated to be 71%.

Comparative Example 1

A hollow-fiber membrane module A similar to that in Example 1 was used. As the priming condition, the flow rate in the vicinity of the outlet port 8b was set to 459 mL/min (linear velocity of 600 cm/min). At this time, the internal pressure value was −58 mmHg, the external pressure value was −28 mmHg, and the pressure difference was 30 mmHg.

Further, the distance between the resin layer parts 7 at both ends of the hollow-fiber membrane module A was 23 cm, and the length of the hollow fiber membrane of which the outside was immersed in a priming liquid was 1 cm.

Therefore, the filling efficiency of the priming liquid was calculated to be 4%. As the concentration condition, the flow rate in the vicinity of the outlet port 8b of the priming liquid was set to 450 mL/min (linear velocity of 588 cm/min), and the filtration rate discharged from the filtrate discharge port 4 was set to 1823 mL/m²/min.

As a result, the treatment time was 364 seconds, the cell recovery rate was 65%, and the survival rate ratio was 95%.

Comparative Example 2

A hollow-fiber membrane module A in which hollow fiber membranes made of polyethersulfone (PES) [trade name: D06-E500-05-N, with a hollow fiber inner diameter of 500 μm, and a fractionation of 500 kD, manufactured by Spectrum Laboratories Inc.] was packed in a cylindrical vessel 1 having a diameter of 6.98 mm and a height of 68 cm provided with a filtrate discharge port 4 and a pressure gauge connection port 15 in the side end part of the cylindrical vessel 1 so that the filtration area is 370 cm², and both ends of a bundle of the hollow fiber membranes 5 were fixed to the inside of the vessel 1 by the resin layer parts 7 was used. The distance between the resin layer parts 7 at both ends at this time was 65 cm. By substituting these values in the Equation 3, the total cross-sectional area of the hollow fiber membranes was calculated to be 0.071 cm².

As the priming condition, the flow rate in the vicinity of the outlet port 8b was set to 2.1 mL/min (linear velocity of 35 cm/min). At this time, the internal pressure value was −55 mmHg, the external pressure value was −89 mmHg, and the pressure difference was 144 mmHg.

Further, the distance between the resin layer parts 7 at both ends of the hollow-fiber membrane module A was 65 cm, and the length of the hollow fiber membrane of which the outside was immersed in a priming liquid was 0 cm.

Therefore, the filling efficiency of the priming liquid was calculated to be 0%.

The conditions of hollow-fiber membrane module, the priming conditions, the concentration conditions, and the performance in Examples 1 to 5 and Comparative Examples 1 and 2 are shown in Table 1. Note that in Examples 6 and 7 and Comparative Example 2, only priming was performed, and cell concentration was not performed.

TABLE 1

| | | Example 1 | Example 2 | Example 3 | Example 4 | Example 5 | Example 6 | Example 7 | Comparative Example 1 | Comparative Example 2 |
|---|---|---|---|---|---|---|---|---|---|---|
| Hollow-fiber membrane module specification | a. Material | PES | PES | PES | PES | PES | ME | ME | PES | PES |
| | b. Inner diameter [mm] | 0.57 | 0.57 | 0.57 | 0.57 | 0.57 | 0.6 | 0.6 | 0.57 | 0.5 |
| | c. Pore diameter | 0.2 μm | 0.2 μm | 0.2 μm | 0.2 μm | 0.2 μm | 0.2 μm | 0.1 μm | 0.2 μm | 500 kD |
| | d. Distance between resin layer parts [cm] | 23 | 23 | 23 | 23 | 23 | 65 | 65 | 23 | 65 |
| | e. Number of fibers [fibers] | 300 | 300 | 300 | 300 | 300 | — | — | 300 | — |
| Priming conditions | f. Linear velocity [cm/min] | 35 | 300 | 420 | 450 | 35 | 35 | 35 | 600 | 35 |
| | g. Internal pressure measurement value [mmHg] | −8 | −32 | −34 | −36 | −8 | −55 | −66 | −58 | −55 |
| | h. External pressure measurement value [mmHg] | −1 | −15 | −12 | −7 | −1 | −46 | −46 | −28 | 89 |
| | i. Pressure difference [mmHg] | 7 | 17 | 22 | 29 | 7 | 9 | 20 | 30 | 144 |
| | j. Length of hollow fiber membrane the outside of which is immersed in priming liquid at the end of priming [cm] | 21 | 17 | 10 | 4 | 21 | 62 | 46 | 1 | 0 |
| | k. Priming liquid filling efficiency [%] | 91 | 74 | 44 | 17 | 91 | 95 | 71 | 4 | 0 |
| Concentration conditions | l. Linear velocity [cm/min] | 588 | 588 | 588 | 588 | 784 | — | — | 588 | — |
| | m. Filtration rate [mL/m2/min] | 1823 | 1823 | 1823 | 1823 | 2422 | — | — | 1823 | — |
| Performance | n. Treatment time [seconds] | 362 | 364 | 365 | 363 | 297 | — | — | 364 | — |
| | o. Cell recovery rate [%] | 86 | 85 | 73 | 70 | 76 | — | — | 65 | — |
| | Cell survival rate ratio [%] | 97 | 96 | 97 | 95 | 98 | — | — | 95 | — |

From the results shown in Table 1, it is apparent that in Examples 1 to 5, by using a priming method in which a priming liquid is filled in a hollow-fiber membrane module in an amount of 15% or more relative to the volume of the hollow-fiber membrane module at a linear velocity of 35 cm/min or more and 450 cm/min or less, the cell concentrate can be produced at a significantly higher cell recovery rate and a significantly higher survival rate ratio as compared with those in Comparative Example 1. In addition, as in Examples 1 to 5, by adjusting the linear velocity at the time of priming to be lower than the linear velocity at the time of concentration, the priming liquid can be easily filled in both the inside and the outside of the hollow fiber membrane, the effective filtration area is enlarged in the subsequent treatment process of the cell suspension, and the recovery rate of cells and the filtration rate can be improved. Further, the cell treatment can be completed while maintaining the closed environment in Examples 1 to 5, therefore, the obtained cells can be provided for therapeutic applications.

In addition, from the results of Examples 3 and 5 shown in Table 1, by decreasing the linear velocity at the time of priming, and increasing the effective filtration area at the time of cell treatment, the filtration rate can be improved without causing the lowering of the cell recovery rate, and as a result, it is expected that the treatment time of the cell suspension is shortened.

In Examples 1 and 6 shown in Table 1, it is indicated that a polysulfone-based or cellulose-based polymer material is more preferably used as the material for a hollow fiber membrane. Further, from the results of Examples 1 and 7 and Comparative Example 2 shown in Table 1, it is indicated that the pore diameter of the pores provided in the wall of the hollow fiber membrane is preferably 0.1 μm or more in a case of performing the priming.

EXPLANATION OF REFERENCE NUMERALS

A, B. Hollow-fiber membrane module
1. Vessel
2. Body part
3. Head part
4, 4'. Filtrate discharge port
5. Bundle of hollow fiber membranes
6. Open end
7. Resin layer part
8a. Inlet port
8b. Outlet port
9. Head part
10. Storage container
11a, 11a'. Pump
11b. Pump
12. Straight stopcock
13. Waste liquid container
14a, 14a'. Internal pressure gauge
14b. External pressure gauge
15. Pressure gauge connection port
16. Circuit
17. Three-way stopcock
18. Recovery container

The invention claimed is:

1. A method for priming a hollow-fiber membrane module in which hollow-fiber membranes are packed in a vessel having an inlet port, an outlet port, and a filtrate discharge port, comprising:
   filling a priming liquid in the hollow-fiber membrane module in an amount of 15% or more relative to a volume of the hollow-fiber membrane module at a linear velocity of 35 cm/min or more and 300 cm/min or less from the inlet port or the outlet port of the hollow-fiber membrane module;
   wherein the inlet port and the outlet port communicate with each other through the inside of the hollow fiber membrane while maintaining a closed environment in the hollow-fiber membrane module.

2. The method according to claim 1, wherein a pressure difference between internal pressure and external pressure of a hollow fiber membrane at the time of priming is 7 mmHg or more and 29 mmHg or less.

3. The method according to claim 2, wherein the internal pressure is negative pressure.

4. The method according to claim 1, wherein the priming liquid is filled in the hollow-fiber membrane module in an amount of 70% or more relative to a volume of the hollow-fiber membrane module.

5. The method according to claim 1, wherein the priming liquid is introduced into the inside of the hollow fiber membrane.

6. The method according to claim 1, wherein the hollow fiber membrane has pores with a pore diameter of 0.07 μm or more and 1.5 μm or less.

7. The method according to claim 1, wherein the priming liquid is at least one selected from the group consisting of physiological saline, infusion, serum, and a culture medium.

8. A method for producing a cell concentrate, comprising:
   after performing the method according to claim 1 using the hollow-fiber membrane module, introducing a cell suspension into the hollow-fiber membrane module from the inlet or the outlet port of the hollow-fiber membrane module, and
   concentrating the cell suspension while discharging a filtrate containing no cells from the filtrate discharge port.

9. The method according to claim 8, wherein the cell suspension is introduced into the hollow-fiber membrane module from the inlet or the outlet port of the hollow-fiber membrane module at a linear velocity of 500 cm/min or more and 2000 cm/min or less.

10. The method according to claim 9, wherein the cell suspension is obtained from the hollow-fiber membrane module through the filtrate discharge port at a filtration rate of 1500 mL/m$^2$/min or more and 3750 mL/m$^2$/min or less.

* * * * *